United States Patent [19]

Gubelmann et al.

[11] Patent Number: 5,066,827

[45] Date of Patent: Nov. 19, 1991

[54] PREPARATION OF METHYLENEDI(PHENYLURETHANE)

[75] Inventors: Michel Gubelmann; Christophew Rochin, both of Lyons; Christian Allandrieu, Villeurbanne, all of France

[73] Assignee: Rhone-Poulenc Chimie, Courbevoie, France

[21] Appl. No.: 545,502

[22] Filed: Jun. 29, 1990

[30] Foreign Application Priority Data

Jun. 29, 1989 [FR] France ................... 89 09001

[51] Int. Cl.$^5$ .......................................... C07C 269/06
[52] U.S. Cl. ....................................... 560/163; 560/25
[58] Field of Search ................... 560/163, 25

[56] References Cited

U.S. PATENT DOCUMENTS 4,266,070 5/1981 May .................... 560/163 X

FOREIGN PATENT DOCUMENTS 3345104 6/1985 Fed. Rep. of Germany .

Primary Examiner—Jose G. Dees
Assistant Examiner—Vera C. Clarke
Attorney, Agent, or Firm—Burns, Doane, Swecker & Mathis

[57] ABSTRACT

Methylenedi(phenylurethane), MDU, is selectively prepared by condensing an alkyl N-phenylcarbamate with a methylenating agent, e.g., formaldehyde or a precursor thereof, in the presence of a catalytically effective amount of the protonic acid, hydrofluoric acid.

11 Claims, No Drawings

PREPARATION OF METHYLENEDI(PHENYLURETHANE)

CROSS-REFERENCE TO COMPANION APPLICATION

Co-pending application Ser. No. 07/545,547, filed concurrently herewith and assigned to the assignee hereof.

BACKGROUND OF THE INVENTION

1. Field of the Invention

The present invention relates to the preparation of methylenedi(phenylurethane), and, more especially, to the preparation of methylenedi(phenylurethane) by a condensation reaction between an alkyl N-phenylcarbamate and a methylenating agent.

2. Description of the Prior Art

Methylenedi(phenylurethane), designated MDU, is an intermediate useful in the production of methylenedi(phenyl isocyanate), designated MDI. Indeed, MDU can be pyrolyzed to MDI in a manner known per se. MDI is a particularly useful starting material for the manufacture of polyurethane foams and elastomers.

MDI is conventionally produced by phosgenation of the diamine which results from the condensation reaction of aniline with formaldehyde. The commercial product is a mixture of various isomers of MDI and oligomers, designated polymethylenedi(phenyl isocyanate), PMDI, from which the pure MDI is isolated.

For obvious reasons associated with the toxicity of phosgene and the disadvantages associated with the production of hydrochloric acid during the phosgenation step, numerous attempts have been made to prepare MDI by processes which do not require a phosgenation step.

Thus, various processes for the preparation of MDI from alkyl N-phenylcarbamates have been proposed to this art which comprise a first step entailing a condensation reaction of the N-phenylcarbamate with formaldehyde to form a mixture containing diphenylmethane dicarbamate and polymethylenedi(phenyl carbamate), higher homologs of methylenedi(phenyl carbamate) (or MDU), followed by a thermal decomposition step.

One of the disadvantages presented by this type of process is that the proportion of dinuclear MDI, and in particular of the 4,4'-isomer, is insufficient.

Another disadvantage presented by this type of process is that, during the condensation reaction step, significant proportions of compounds such as N-carboalkoxyanilinophenylmethanes, bis(N-carboalkoxyanilino)methanes and N,N'-dicarboalkoxyaminobenzylanilines, as well as their higher condensation derivatives, are formed together with the desired diphenylmethane dicarbamate. These various impurities are problematical in the conversion of the reaction mixture to the desired diisocyanates.

In U.S. Pat. No. 4,146,727 it has been proposed to rearrange impurities of the N-benzyl type of formula (I):

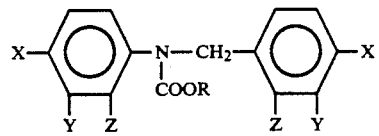

in which X, Y, or Z can represent, in particular, a -NHCOOR group and R is an alkyl group having from 1 to 3 carbon atoms, their dimers, trimers, tetramers, etc., into diphenylmethane dicarbamate by contacting them, at a temperature ranging from 50° to 170° C. and preferably from 80° to 130° C., with a catalytically effective amount of a strong protonic acid medium.

Thus, a supplementary step would have to be carried out in order to at least partially suppress such impurities.

In published French Patent Application No. 2,460,972 (corresponding to U.S. Pat. No. 4,319,018) it is proposed to carry out the step involving the condensation reaction of the alkyl N-phenylcarbamate and formaldehyde, or a precursor material generating formaldehyde, in the simultaneous presence of at least one compound selected, in particular, from among bis(N-carboalkoxyanilino)methanes and N,N'-dicarboalkoxyaminobenzylanilines and an aqueous acid solution, the concentration of which is adjusted such that the reaction kinetics are acceptable and secondary reactions are maintained at a minimum level, at a temperature ranging from 10° to 150° C. and preferably from 20° to 120° C.

This process, however, does not permit the removal of all of the impurities under consideration.

Hence, serious need exists in this art for a one-stage process for the preparation of methylenedi(phenylurethane) by a condensation reaction between an alkyl N-phenylcarbamate and a methylenating agent and having an improved selectivity for methylenedi(phenylurethane). Need also exists for a process that permits the proportion of the 4,4'-isomer in the difunctional product to be controlled.

SUMMARY OF THE INVENTION

Accordingly, a major object of the present invention is the provision of an improved process for the preparation of methylenedi(phenylurethane) by a condensation reaction between an alkyl N-phenylcarbamate and a methylenating agent in the presence of a protonic acid, wherein the protonic acid is hydrofluoric acid.

DETAILED DESCRIPTION OF THE PREFERRED EMBODIMENTS OF THE INVENTION

More particularly according to the present invention, suitable alkyl N-phenylcarbamates for the subject process are those in which the alkyl (or cycloalkyl) moiety has from 1 to 6 and preferably from 1 to 4 carbon atoms. Ethyl N-phenylcarbamate is an especially preferred starting material for the process of this invention.

According to the present invention, by "methylenating agent" is intended formaldehyde or compounds capable of liberating formaldehyde under the reaction conditions, such as paraformaldehyde, trioxane, dialkoxymethanes, in particular methylal, and urotropin (hexamethylenetetramine). Preferably, formaldehyde, paraformaldehyde, trioxane or methylal is used.

The stoichiometry of the condensation reaction to form methylenedi(phenylurethane) indicates the presence of 2 moles of alkyl N-phenylcarbamate per mole of methylene (—$CH_2$—) groups. Nonetheless, it is advantageous to use the alkyl N-phenylcarbamate in excess relative to the stoichiometry, without it being beneficial that the molar ratio of alkyl N-phenylcarbamate/-$CH_2$- be greater than 10. This ratio preferably ranges from 3 to 7.

The process according to the invention requires the presence of hydrofluoric acid. It is advantageous to use anhydrous hydrofluoric acid. When the methylenating agent is formaldehyde, trioxane or performaldehyde, water is produced during the condensation reaction and could present problems in the recovery of the hydrofluoric acid, without otherwise interfering with the reaction under consideration.

When the methylenating agent is a dialkoxymethane, an alcohol is produced during the condensation reaction, which alcohol is inert under the conditions of the reaction and can easily be separated from hydrofluoric acid.

The amount of hydrofluoric acid to be used is not critical. Hydrofluoric acid can be employed in a significant amount relative to the reactants, such that it constitutes the solvent in the reaction mixture. The hydrofluoric acid can also be present in lesser amounts.

To advantageously carry out the process of this invention, the molar ratio of hydrofluoric acid to alkyl N-phenylcarbamate is at least 5 and preferably is less than 20.

The reaction temperature, in general, advantageously ranges from $-20°$ to $80°$ C.

Preferably, the process of the present invention is carried out at a temperature ranging from 0 to $60°$ C. Indeed, above $60°$ C. a reduction in the proportion of the 4,4′-isomer of methylenedi(phenylurethane), an increase in derivatives containing 3 aromatic rings and an isomerization of the 4,4′-isomer to the 2,4′-isomer are simultaneously observed.

It is also observed, below $60°$ C., that the proportion of derivatives having 3 aromatic rings remains low in the reaction mixture and that, the lower the temperature, the higher is the proportion of the desired 4,4′-isomer in the methylenedi(phenylurethane) produced.

The pressure is not an essential process parameter. However, when the reaction temperature is higher than $20°$ C., it is preferable to operate under a pressure greater than atmospheric pressure in order to maintain the hydrofluoric acid in liquid state.

The process according to the invention can be carried out in hydrofluoric acid as the reaction solvent, or in a mixture of hydrofluoric acid and an organic solvent. Exemplary such organic solvents include aliphatic hydrocarbons such as hexane and heptane; alicyclic hydrocarbons such as cyclohexane and methylcyclohexane; and halogenated hydrocarbons such as chloroform, methylene chloride, ethylene chloride, chlorocyclohexane, perchlorocyclohexane, chlorobenzene and dichlorobenzene. When a solvent of this type is used, it constitutes at most 300% and preferably from 10% to 150% by weight relative to the alkyl N-phenylcarbamate employed. The reaction time can vary over wide limits; it generally ranges from 15 min to 8 hours.

The reaction can be carried out discontinuously or continuously.

Upon completion of the reaction or of the permitted reaction time, the desired final product is recovered by any appropriate means, for example by evaporation of the hydrofluoric acid.

In order to further illustrate the present invention and the advantages thereof, the following specific examples are given, it being understood that same are intended only as illustrative and in nowise limitative.

In said examples, the following conventions are employed:

(i) MDU YLD(%): represents the yield of methylenedi(ethyl carbanilate) calculated relative to the initial number of moles of —$CH_2$— groups;

(ii) 3-Ph(%): represents the yield (YLD) of compounds having 3 aromatic rings, calculated in like manner;

(iii) 4,4′-: represents methylene-4,4′-di(ethyl carbanilate) of the formula:

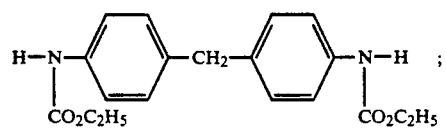

(iv) 2,4′-: represents methylene-2,2′-di(ethyl carbanilate);

(v) A represents bis(N-carboethoxyanilino)methane of the formula:

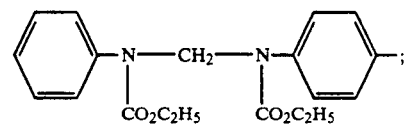

(vi) B represents N,N′-dioarboethoxyaminobenzylanilines of the formula:

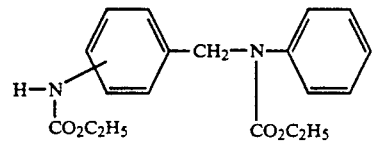

EXAMPLES 1 to 3

The following materials were charged into a Hastelloy reactor having a capacity of 50 cc, fitted with a magnetic stirrer:

(i) 50 mmoles of ethyl phenylcarbamate,
(ii) 2 mmoles of trioxane (equal to 6 mmoles of —$CH_2$— groups), and
(iii) 20 cc (1 mole) of anhydrous hydrofluoric acid, or x cc of methylene chloride and (iv) (20-x) cc of anhydrous hydrofluoric acid.

At the end of the experiment the reaction mixture was analyzed by gas phase and liquid phase chromatography.

The particular conditions and the results obtained after a reaction time of 2 hours at $40°$ C. are reported in Table I below:

TABLE I

| Example No. | HF (cc) | $CH_2Cl_2$ (cc) | MDU YLD (%) | Distribution of isomers (%) | | 3-Ph (%) |
|---|---|---|---|---|---|---|
| | | | | 4,4′- | 2,4′- | |
| 1 | 20 | 0 | 81.5 | 90 | 10 | 0 |
| 2 | 10 | 10 | 97.7 | 91 | 9 | 2.5 |

TABLE I-continued

| Example No. | HF (cc) | CH$_2$Cl$_2$ (cc) | MDU YLD (%) | Distribution of isomers (%) | | 3-Ph (%) |
|---|---|---|---|---|---|---|
| | | | | 4,4'- | 2,4'- | |
| 3 | 5 | 15 | 97.7 | 91 | 9 | 2 |

The presence of impurities containing a methyleneamino linkage was not detected in these examples.

{YLD(A)= YLD(B)=0}

EXAMPLES 4 and 5

The procedure of Example 1 was repeated, except that the reaction temperature was modified The particular conditions and the results obtained are reported in Table (II) below:

TABLE II

| Example No. | T °C. | MDU YLD (%) | Distribution of isomers | | 3Ph (%) |
|---|---|---|---|---|---|
| | | | 4,4'- | 2,4'- | |
| 1 | 40 | 81.5 | 90 | 10 | 0 |
| 4 | 20 | 80 | 94 | 6 | 0 |
| 5 | 0 | 75 | 96 | 4 | 0 |

The presence of impurities containing a methyleneamino linkage was not detected in these examples.

{YLD(A)= YLD(B)=0}

EXAMPLE 6

The procedure of Example 4 above was repeated, but replacing the trioxane by an equivalent amount of methylene groups in the form of dimethoxymethane (6 mmoles).

The results were as follows:
MDU YLD(%) : 83.
Distribution of isomers (%).
(a) 4,4'- : 94
(b) 2,4'- : 6
(c) 3-Ph (%) : 0

The presence of impurities containing a methyleneamino linkage was not detected in this example.

{YLD(A)= YLD(B)=0}

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. In a process for the preparation of methylenedi(phenylurethane) by condensing an alkyl N-phenylcarbamate with a methylenating agent in the presence of a catalytically effective amount of a protonic acid, the improvement which comprises utilizing as the protonic acid catalyst therefor, hydrofluoric acid.

2. The process defined by claim 1, comprising conducting said condensation reaction in liquid phase.

3. The process as defined by claim 1, wherein the molar ratio of alkyl N-phenylcarbamate —CH$_2$— ranges from 3 to 7.

4. The process, as defined by claim 1, said methylenating agent is formaldehyde, paraformaldehyde, trioxane or methylal.

5. The process as defined by claim 1, said alkyl N-phenylcarbamate is ethyl N-phenylcarbamate.

6. The process as defined by claim 1, carried out in the presence of an organic reaction solvent.

7. The process as defined by claim 6, said organic solvent is methylene chloride.

8. The process as defined by claim 1, wherein the molar ratio of HF/alkyl N-phenylcarbamate is greater than or equal to 5.

9. The process as defined by claim 8, wherein the molar ratio of HF/alkyl N-phenylcarbamate is less than or equal to 20.

10. The process as defined by claim 1, carried out at a reaction temperature ranging from 0° to 60° C.

11. The process as defined by claim 1, said protonic acid is anhydrous hydrofluoric acid.

* * * * *